United States Patent [19]

Kaneko et al.

[11] Patent Number: 4,864,048
[45] Date of Patent: Sep. 5, 1989

[54] PROCESS FOR PREPARING PHOSPHONITRILE COMPOUND HAVING SUBSTITUTED HYDROXYL GROUP

[75] Inventors: Masaharu Kaneko, Kitaibaragi; Kazuhiko Fujikawa; Tetsuhiko Okamoto, both of Tokyo, all of Japan

[73] Assignee: Shin Nisso Kako Co., Ltd., Tokyo, Japan

[21] Appl. No.: 82,336

[22] Filed: Aug. 6, 1987

[30] Foreign Application Priority Data

Aug. 9, 1986 [JP] Japan ................................ 61-186139

[51] Int. Cl.$^4$ ................................................ C07F 9/24
[52] U.S. Cl. ................................................ 558/93
[58] Field of Search ................................ 558/80, 93

[56] References Cited

U.S. PATENT DOCUMENTS

| | | | |
|---|---|---|---|
| 3,193,571 | 7/1965 | Bilger | 558/93 |
| 3,394,205 | 7/1968 | Bilger | 558/93 |
| 3,839,513 | 10/1974 | Patel | 558/80 |
| 4,571,310 | 2/1986 | Tanino | 558/93 |

FOREIGN PATENT DOCUMENTS 59-0216895  6/1984  Japan ................................ 558/93

*Primary Examiner*—William R. Dixon, Jr.
*Assistant Examiner*—Margaret B. Medley
*Attorney, Agent, or Firm*—Lowe, Price, LeBlanc, Becker & Shur

[57] ABSTRACT

A process for preparing a phosphonitrile compound having a substituted hydroxyl group by making use of a phosphonitrile chloride oligomer and an alcohol as the starting materials, which comprises:

(1) a first step of reacting said phosphonitrile chloride oligomer with said alcohol in a specific amount ratio of the active chlorine contained in said phosphonitrile chloride oligomer relative to the alcohol in the presence of a specific amount of a tertiary amine at a specific temperature, thereby substituting a specific amount of said active chlorine by a substituted alkoxy group, (2) a second step of elevating the temperature of the reaction mixture obtained in the first step to a specific temperature to cause a condensation reaction through the elimination of R—Cl, and (3) a third step of adding an alcohol in a specific amount ratio relative to said active chlorine which remains at the stage of completion of the second step, to the reaction system, and making said remaining active chlorine react with said alcohol while supplying ammonia in a specific amount ratio or more relative to the amount of said active chlorine which has been originally contained in said phosphonitrile chloride oligomer into the reaction system, thereby substantially completely and substituting said remaining active chlorine by a substituted hydroxyl group.

21 Claims, No Drawings

PROCESS FOR PREPARING PHOSPHONITRILE COMPOUND HAVING SUBSTITUTED HYDROXYL GROUP

BACKGROUND OF THE INVENTION

1. FIELD OF THE INVENTION

This invention relates to a novel process for preparing a phosphonitrile oligomer having a substituted hydroxyl group. More particularly, the present invention is concerned with a novel process for preparing a mixture of a phosphonitrile oligomer represented by the following general formula:

(I)

(wherein n is an integer of 3 or more, and
R is
(i) a straight-chain or branched chain alkyl group containing or not containing a halogen atom or an alkoxy group,
(ii) a straight-chain or branched chain alkenyl group,
(iii) a straight-chain or branched chain alkinyl group,
(iv) an aralkyl group containing or not containing a halogen atom, an alkyl group, or an alkoxy group,
(v) a cycloalkyl group)
with a poly(phosphonitrile oligomer) obtained by condensing said phosphonitrile oligomer.

The poly(phosphonitrile oligomer) is a compound represented by, e.g., the following general formula:

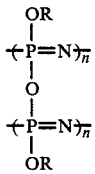
(II)

and is finding industrial applications including uses as flame retardants, heat-resistant agents, lubricating agents, and electro-insulating agents, etc.

2. DESCRIPTION OF THE PRIOR ART

Alkoxyphosphonitrile oligomers and poly(alkoxyphosphonitrile oligomers) produced by condensing said alkoxyphosphonitrile oligomers are finding wide applications including use in various industrial materials by virtue of their excellent heat-resistance, cold-resistance, lubricity, electro-insulation and chemical stability.

The said alkoxyphosphonitrile oligomer is obtained by alkoxylation of phosphonitrile chloride oligomer having a cyclic or linear structure represented by the formula:

(III)

(wherein n is defined above), particularly cyclic phosphonitrile chloride oligomers represented by the formula:

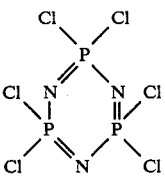
(IV)

(wherein n is 3), and cyclic phosphonitrile chloride oligomers represented by the formula:

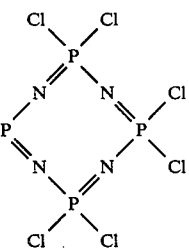
(V)

(wherein n is 4) and mixture composed mainly of said two kinds of phosphonitrile chloride oligomer.

Further, a mixture of an alkoxyphosphonitrile oligomer with a poly(alkoxyphosphonitrile oligomer) has drawn particular attention as a flame retardants for rayon and other various organic high-molecular substances.

Various processes have been proposed for producing such a mixture. Examples of the processes include (1) one as described in Japanese Patent Laid-Open No. 109320/1974 which uses a tertiary amine as an acid acceptor and (2) one as described in Japanese Patent Laid-Open No. 216895/1984 (corresponding to U.S. Pat. No. 4,571,310) which is an improved process of the above process (1).

(1) Process described in Japanese Patent Laid-Open No. 109320/1974:

This process comprises reacting a phosphonitrile chloride oligomer with an alcohol in the presence of an acid acceptor comprised of a tertiary amine, such as pyridine or triethylamine, to produce a compound in which a chlorine atom still remains in the nucleus of the phosphonitrile chloride oligomer, i.e., a partially alkoxylated phosphonitrile oligomer, and heating this compound in the presence of a tertiary amine to form a linkage represented by the abovementioned general formula (II).

In this process, the amount of the remaining active chlorine which is still contained in the alkoxyphosphonitrile oligomer at the stage of the completion of the first step is small (e.g., about 1% to about 15%). Therefore, in order to complete the condensation reaction in the presence of the tertiary amine in a short time (e.g., 5.5 hr), it is necessary to conduct the condensation reaction at a high temperature (e.g., about 100° C.) (see Examples 1, 4, 5, and 6). This makes it impossible to suppress the excessive condensation. On the other hand, the practice of the condensation reaction at a low temperature (e.g., about 30° C. to about 35° C.) is disadvantageous from the standpoint of industry, because it takes a prolonged period of time, i.e., as long as 18 hrs (see Example 2). In this process, when the temperature of the condensation reaction exceeds 60° C., a substance in which an OH group is bonded to a phosphorus atom in the phosphonitrile is produced as a by-product, which deteriorates the quality of the final product as will be mentioned later.

(2) Process described in Japanese Patent Laid-Open No. 216895/1984:

This process aims at producing a phosphonitrile compound having an alkoxy group using phosphonitrile chloride oligomer and an alcohol as starting materials, and comprises:

(A) a first step of making the phosphonitrile chloride oligomer react with "an" alcohol in an amount of 0.2 to 0.8 equivalent per equivalent amount of the active chlorine contained in the phosphonitrile chloride oligomer in the presence of an organic tertiary amine in an equivalent amount or more relative to the amount of the alcohol at a temperature of 20° C. or below to substitute 34 to 75% of the active chlorine by an alkoxy group, (B) a second step of elevating the temperature of the reaction mixture obtained in the first step to cause a condensation reaction through the elimination of an alkyl chloride, and (C) a third step of adding an alcohol to the reaction system obtained above in an at least equivalent amount relative to the amount of the active chlorine which remains at the stage of completion of the second step to the reaction system obtained in the second step to cause a reaction of the alcohol with the active chlorine, thereby the remaining active chlorine is substantially completely substituted by an alkoxy group.

According to this method, the amount of the remaining active chlorine in the alkoxyphosphonitrile at the stage of completion of the first step is large, which not only makes it possible to smoothly progress the condensation reaction in the second step even at a temperature of 60° C. or below but also makes it possible to progress the condensation reaction while determining the degree of condensation and to cease the condensation reaction at will based on the result of the determination. However, in this method, products which are considerably easily soluble in water are frequently produced, although this method intends to produce a phosphonitrile compound having an extremely low solubility in water. This is because the reaction product contains a large amount of an oligomer comprised of a phosphonitrile unit having an OH group represented by the following formula:

The oligomer having an OH group such as one represented by the above formula (VI) has a high solubility in water, which renders the product containing it considerably soluble in water. When a mixture containing a phosphonitrile compound which is considerably easily soluble in water is added to, e.g., a viscose solution in preparing a nonflammable rayon, part of the phosphonitrile oligomer or poly(phosphonitrile oligomer) having an OH group is dissolved in a spinning bath, which makes it impossible to impart an intended flame retardance to the rayon. Further, the rayon containing a phosphonitrile compound which is considerably easily soluble in water is unfaborable for practical use, because the flame retardance is remarkably lowered when it is repeatedly washed.

SUMMARY OF THE INVENTION

In accordance with the present invention, there is provided a process for preparing a phosphonitrile compound having a substituted hydroxyl group by using a phosphonitrile chloride oligomer and an alcohol as the starting materials, which comprises:

(1) a first step of making said phosphonitrile chloride oligomer react with said alcohol in a specific amount ratio to the active chlorine contained in said phosphonitrile chloride oligomer in the presence of a tertiary amine of a specific amount relative to the alcohol at a specific temperature, thereby substituting a specific amount of said active chlorine by a substituted alkoxy group, (2) a second step of elevating the temperature of the reaction mixture obtained in the first step to a specific temperature to cause a condensation reaction through the elimination of R—Cl, and (3) a third step of adding an alcohol in a specific amount ratio relative to said active chlorine which remains at the stage of completion of the second step of the reaction system, and making said remaining active chlorine react with said alcohol while supplying ammonia in a specific amount ratio or more relative to the amount of said active chlorine which has been originally contained in said phosphonitrile chloride oligomer into the reaction system, thereby the remaining active chlorine is substantially completely substituted by an alkoxy group.

DETAILED DESCRIPTION OF THE INVENTION

An object of the present invention is to provide a process for preparing a mixture comprised of a substituted oxyphosphonitrile oligomer and a poly(substituted oxyphosphonitrile oligomer) each substantially free from an OH group which has an adverse effect on the product.

Another object of the present invention is to provide a process for preparing a mixture comprised of a substituted oxyphosphonitrile oligomer and a poly(substituted oxyphosphonitrile oligomer) each substantially free from an OH group and having arbitrary viscosity and molecular weight distribution at low cost with ease and excellent reproducibility.

Description of the Process of the Present Invention

The present inventors have found that the formation of a phosphonitrile oligomer containing a phosphonitrile unit having an OH group as represented by the above formula (VI) by the production of a mixture of a substituted oxyphosphonitrile oligomer with a poly(substituted oxyphosphonitrile oligomer) from a phosphonitrile chloride oligomer using a tertiary amine is attributed to the action of a tertiary amine hydrochloride at a temperature of about 60° C. or above, which has been produced from the tertiary amine used as acid acceptor. The present invention has been made based on this finding.

Specifically, the present inventors have found that although the tertiary amine serves as an acid acceptor in a reaction of the remaining active chlorine with the alcohol in the third step which will be described later, the hydrochloride of the tertiary amine which is produced with the progress of the reaction breaks a —P—O—P— linkage formed in the second step in cooperation with the hydrochloride which has been already formed in the first step, which results in the formation of a phosphonitrile oligomer containing a phosphonitrile unit having an OH group.

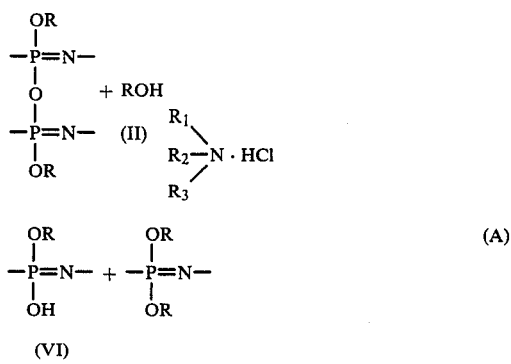

(wherein

is a tertiary amine).

Further, the present inventors have found that the introduction of ammonia into the reaction system in the third step brings about the following phenomena.

(1) The hydrochloride of the tertiary amine present in the third step is converted in a corresponding tertiary amine. This conversion prevents the formation of the phosphonitrile oligomer containing the phosphonitrile unit having an OH group (VI) caused by a reaction represented by the above-mentioned reaction formula (A) and, at the same time, smoothly progresses the substitution reaction of the remaining active chlorine with the substituted hydroxyl group (RO- group) due to the presence of the tertiary amine and ammonia.

(2) When the amount of the remaining active chlorine is ½ or less of the amount of the active chlorine contained in the phosphonitrile chloride oligomer used as the starting material, the P—NH$_2$ linkage which may be formed by a direct reaction of the remaining active chlorine with ammonia, is not formed unless the reaction is conducted under elevated pressure.

Specifically, the present invention is directed to a process for preparing a phosphonitrile compound having a substituted hydroxyl group by reaction of a phosphonitrile chloride oligomer with an alcohol represented by the following general formula:

ROH (wherein R is:
1 a straight-chain or branched chain alkyl group containing or not containing a halogen atom or an alkoxy group,
2 a straight-chain or branched chain alkenyl group,
3 a straight-chain or branched chain alkinyl group,
4 an aralkyl group containing or not containing a halogen atom, an alkyl group, or an alkoxy group, or
5 a cycloalkyl group),
which comprises:
(1) a first step of adding said alcohol to said phosphonitrile chloride oligomer in an amount of 0.2 to 0.8 equivalent per equivalent amount of the active chlorine contained in the phosphonitrile chloride oligomer and making them react with each other in the presence of a tertiary amine in an equivalent amount or more relative to the amount of said alcohol at a temperature of 20° C. or below, thereby substituting 34 to 75% of the active chlorine by an RO-group, (2) a second step of elevating the temperature of the reaction mixture obtained in the first step to cause a condensation reaction through the elimination of R—Cl at a temperature ranging from 20° C. to 60° C., and (3) a third step of adding an alcohol in an at least equivalent amount relative to the amount of the active chlorine which remains at the stage of completion of the second step to the reaction system obtained in the second step and then making said alcohol react with said remaining active chlorine while supplying ammonia into the reaction system, thereby substantially and completely substituting the remaining active chlorine by said RO-group.

The term "tertiary amine in an equivalent amount relative to the alcohol" as used herein is intended to mean 1 mol of tertiary amine per mol of —OH group contained in the alcohol.

Further, the term "active chlorine" as used herein is intended to mean a chlorine atom which is bonded to a phosphorus atom contained in a phosphonitrile oligomer or its polymer.

The characteristic features of the present invention will now be summarized.

(Starting Materials)

(1) Phosphonitrile Chloride Oligomer:

The phosphonitrile chloride oligomer is obtained in the form of a mixture of various compounds represented by the general formula (III) through a reaction of phosphorus pentachloride with ammonium chloride. In the present invention, the mixture as produced may be used as the starting material, or the mixture may be separated into a plurality of compounds by a suitable method (e.g., a method as described in Japanese Patent Publication No. 2608/1986). The phosphonitrile chloride oligomers which have been isolated by such a method and represented by the formulae (IV) and (V) may be used alone or in the form of a mixture thereof as the starting material according to the purpose of applications where the final product of the present invention is used.

(2) Alcohol:

Although examples of the alcohol which may be used in the present invention include the following, it is not limited to these only:

① saturated aliphatic alcohols such as methanol, ethanol, propanol (including various isomers thereof), butanol (including various isomers thereof), pentanol (including various isomers thereof), octanol (including various isomers thereof), and trifluoroethanol;

② unsaturated alcohols such as allyl alcohol and propargyl alcohol;

③ aralkyl alcohols such as benzyl alcohol, chlorobenzyl alcohol, methylbenzyl alcohol, and methoxybenzyl alcohol; and ④ alicyclic alcohols such as cyclohexanol.

In the present invention, the alcohol used in the first step is not necessary the same as the alcohol used in the third step. Furthermore, if necessary, a mixture of two or more alcohols may be used in each of the first and third steps.

(3) Tertiary Amine:

Although examples of the tertiary amine which may be used in the present invention include the following tertiary amines, they are not limited to these only:

1 aliphatic amines:
triethylamine,
tripropylamine,
tributylamine,
trioctylamine,
N-methyl-N-ethylpropylamine, and
N,N-diethylpropylamine;
2 alicyclic amines N,N-dimethylcyclohexylamine;
3 aromatic amines:
N,N-dimethylaniline,
N,N-diethylaniline,
N,N-diethyltoluidines;
4 aralkylmines:
N,N-dimethylbenzylamine; and
5 heterocyclic amines:
triethylenediamine,
quinuclidine,
N-methylpyrrolidine,
N-methylpiperidine,
N,N'-dimethylpiperidine,
pyridine,
alpha-picoline,
beta-picoline,
gamma-picoline,
5-ethyl-2-picoline, and
trimethylpyridine.

These tertiary amines are used alone or in the form of any mixture thereof.

(Organic Solvent)

It is preferable that the present invention be practiced in an inactive organic solvent. Examples of such a solvent include benzene, toluene, xylene, monochlorobenzene, tetrahydrofuran, and dioxane. However, the organic solvent is not limited to them.

(First Step)

In the first step, the alcohol is used in an amount ranging from 0.2 to 0.8 equivalent per equivalent of the active chlorine contained in the phosphonitrile chloride oligomer, and the reaction is conducted at a temperature of 20° C. or below in order to suppress the elimination of R—Cl. By virtue of these expedients, the amount of the remaining active chlorine at the stage of completion of the first step is much larger than that attained by the process as described in the above-mentioned Japanese Patent Laid-Open No. 109320/1974.

Further, in the first step, only the substitution of the substituted hydroxyl group for the active chlorine occurs, and no condensation reaction is substantially caused. This is extremely convenient for stepwise progression of all the reactions of the present invention while controlling the whole reactions.

(Second Step)

In the present invention, the condensation reaction of the phosphonitrile oligomers through the elimination of R—Cl is conducted at a temperature lower than that adopted in conventional processes. This condition of temperature not only makes it easy to control the degree of condensation but also prevents the poly(substituted oxyphosphonitrile oligomer) obtained by the condensation reaction from decomposition with the tertiary amine hydrochloride. The reason why the condensation reaction of the phosphonitrile oligomers through the elimination of R—Cl can be conducted at a low temperature resides in that a large amount of the active chlorine remains at the stage of completion of the first step. It is noted in this connection that when 34 to 75% of the active chlorine contained in a phosphonitrile chloride oligomer is substituted with a substituted hydroxyl group, the amount of the remaining active chlorine in the phosphonitrile compound is 16 to 40% by weight in the case where the substituted hydroxyl group is a propoxy group.

(Third Step)

In the third step, gaseous ammonia is blown into the reaction system. This reconverts the tertiary amine hydrochloride which is a by-product of the reaction formed prior to the third step to the original tertiary amine. Therefore, the substitution reaction with the substituted hydroxyl group can exclusively be progressed without causing the decomposition of the poly(-substituted oxyphosphonitrile oligomer) with the tertiary amine hydrochloride even at a temperature of 60° C. or above.

In the third step, the condensation reaction does not substantially proceed, and only the substitution of the substituted hydroxyl group for the remaining active chlorine proceeds substantially quantitatively.

There is a possibility that a part of the remaining active chlorine is substituted with an $NH_2$ group by blowing ammonia into the reaction system. However, as mentioned above, when the amount of the remaining active chlorine is ½ or less of the amount of the active chlorine which has been originally contained in the phosphonitrile chloride oligomer, no substitution of the $NH_2$ group for the remaining active chlorine is caused as far as the reaction is conducted under atmospheric pressure. The amount of the remaining active chlorine at the stage of completion of the second step varies depending upon the degree of condensation. However, when the substituted hydroxyl group is a propoxy group, the amount of the remaining active chlorine at the stage of completion of the second step is 15 to 20% by weight based on the whole phosphonitrile compound, and calculating based on $PNCl_2$ which is a unit of the phosphonitrile chloride, the substitution ratio of the propoxy group with respect to two active chlorine atoms is 1.2 to 1.4. Therefore, the amount of the remaining active chlorine is surely less than ½ of the amount of the active chlorine which has been originally contained in the phosphonitrile chloride oligomer. Further, the infrared spectrum analysis or nuclear magnetic resonance analysis of the final product obtained according to the present invention reveals that the product is free from the $NH_2$ group.

(Procedures)

The process of the present invention is practiced, for example, as follows.

In the first step, appropriate amounts of an alcohol and a tertiary amine are added to a suitable solvent to prepare a solution. A 20 to 40% phosphonitrile chloride oligomer solution prepared by dissolving the phosphonitrile chloride oligomer in a suitable solvent is added drop by drop to the above-prepared solution at a temperature of 20° C. or below, preferably 10° C. or below, more preferably about 0° C. with stirring. When the temperature is above 20° C., the condensation reaction due to the elimination of R—Cl is caused unfavorably.

Although the time required for dropwise addition is not particularly limited, it is preferably 1 to 2 hours.

The amount of the alcohol used in the first step is in the range of 0.2 to 0.8 equivalent per equivalent of the active chlorine contained in the phosphonitrile chloride oligomer depending upon the degree of condensation or molecular weight distribution required in the final product. The added alcohol is surely consumed only for the alkoxylation reaction. The amount of the tertiary amine is one equivalent or more per equivalent of the alcohol used. The use of an excessive amount of the tertiary amine is effective in accelerating the reaction. However, the use of the tertiary amine in an amount of two equivalents or more is meaningless from the standpoint of economy.

The second step in conducted by elevating the reaction temperature after the completion of the first step. The purpose of practicing this step is to cause a condensation reaction due to the elimination of R—Cl. The temperature of the second step is in the range of 20° to 60° C., preferably 30° to 35° C. depending upon the desired degree of condensation and molecular weight distribution of the final product. When the temperature is above 60° C., the decomposition reaction of the poly-(alkoxyphosphonitrile oligomer), i.e., a condensation product, represented by the reaction formula (A) is also significantly progressed, which results in the formation of a compound having an OH group bonded to the phosphonitrile nucleus. The formation of such a hydroxy containing compound has an adverse effect on the performance of the product intended in the present invention as a flame retardant. Therefore, a temperature exceeding 60° C. is not adopted in the present invention.

The reaction product in the second step is analyzed by gel permeation chromatography (hereinafter abbreviated as "GPC"), and the reaction is ceased at a point where a desired molecular weight distribution is attained. In general, the reaction time in the second step is preferably 6 to 8 hours at a temperature of 30° to 35° C.

In the third step, an alcohol is added to the reaction system in an amount of at least one equivalent, preferably at least 1.5 equivalents per equivalent of an active chlorine remaining at the stage of completion of the second step. Then, gaseous ammonia is blown into the reaction system in an amount of at least one equivalent, preferably 1.1 to 1.5 equivalents per equivalent of the active chlorine which has been originally contained in the phosphonitrile chloride oligomer. The reaction is progressed as the gaseous ammonia is blown into the reaction system. Although the time required for blowing the ammonia is not limited, it is preferred that the ammonia be blown for 3 to 4 hours. As the ammonia is blown into the reaction system, the tertiary amine hydrochloride formed prior to the third step is rapidly converted into a tertiary amine and ammonium chloride, and finally substantially the whole of the tertiary amine hydrochloride disappears from the reaction system. Therefore, even when the reaction temperature in the third step exceeds 60° C., the decomposition reaction of the poly(substituted oxyphosphonitrile oligomer) formed in the second step is substantially and completely prevented.

In order to avoid the condensation reaction which may be caused as a side reaction in the third step, it is preferred that the reaction is conducted at a temperature ranging from 20° to 50° C. for a long period of time (e.g., 40 hours), thereby completing the substitution of the substituted hydroxyl group for the chlorine atom. However, little or no condensation reaction takes place even when the reaction temperature is further elevated to complete the reaction after the reaction is conducted at a temperature of 20° to 50° C. for 6 to 10 hours.

After completion of the third step, the reaction mixture is degassed under a slightly reduced pressure to remove the excess ammonia. Thereafter, the excess alcohol, free tertiary amine and organic solvent are recovered by distillation under reduced pressure. A water immiscible inactive solvent is added to the residue of distillation, and the resulting liquid is then washed several times with water to remove ammonium chloride. A desiccant is added to the washed liquid to dry the liquid. Then, the solvent is distilled off thoroughly. Thus, an intended product according to the present invention, i.e., a substituted oxyphosphonitrile compound, is obtained. This compound is obtained usually in the form of a liquid having a pale yellow color.

The substituted oxyphosphonitrile compound thus obtained exhibits excellent performance when it is used as a flame retardant. The recovered tertiary amine, alcohol, and organic solvent can be reused as such or after purification by a suitable method.

ADVANTAGE OF THE INVENTION

According to the present invention, each reaction can be easily controlled, and the decomposition reaction of the —P—O—P— linkage with the tertiary amine hydrochloride can also be suppressed, which makes it possible to prepare a mixture comprised of a substituted oxyphosphonitrile oligomer and a poly(substituted oxyphosphonitrile oligomer) having a desired degree of condensation and molecular weight distribution and each substantially free from an OH group causative of an increase in the solubility in water.

The mixture is not only substantially free from the active chlorine (content: about 0.5% by weight or less) but is also free from an —NH$_2$ group, the presence of which is expected from the use of an ammonia gas.

Another great advantage of the present invention resides in that the use of ammonia in the third step contributes to a reduction in the amount of the expensive tertiary amine to be used. When ammonia is not used, the tertiary amine should be used in an amount of at least one equivalent as a whole per equivalent amount of the active chlorine which has been originally contained in the phosphonitrile chloride oligomer. On the other hand, when ammonia is used, the amount of the tertiary amine to be used can be reduced to one equivalent per equivalent of the active chlorine which is reacted with the alcohol in the first step, although the reaction should be prolonged.

When an industrial production is taken into consideration, it is needless to say that the tertiary amine which is in the form of a hydrochloride should be reconverted to a free tertiary amine for repeated use. However, the process of the present invention does not require a separate treatment of such a step, because in the present invention the step of reconverting the free tertiary amine from the tertiary amine hydrochloride is involved in the third step.

The substituted oxyphosphonitrile compound prepared according to the present invention exhibits excellent performance when it is used as a flame retardant.

EMBODIMENT OF THE INVENTION

The following examples illustrate the present invention but should not be construed as limiting the scope of the present invention.

EXAMPLE 1

(First Step)

116.0 g (1 mol, calculated on $NPCl_2$) of a mixture of phosphonitrile chloride oligomer which had been synthesized by a reaction of phosphorus pentachloride with ammonium chloride according to a customary method (a mixture comprised of 58.2% by weight of cyclic triphosphonitrile chloride, 15.9% by weight of cyclic tetraphosphonitrile chloride, and 25.9% by weight of other phosphonitrile chloride oligomers) was dissolved in 215.4 g of monochloro benzene to prepare a 35.0% by weight solution of a phosphonitrile chloride oligomer mixture in monochlorobenzene.

60.0 g (1 mol) (0.5 equivalent relative to amount of the active chlorine contained in the phosphonitrile chloride oligomer) of n-propyl alcohol, 118.7 g (1.5 equivalents relative to the amount of n-propyl alcohol) of pyridine were charged into a 1-l four-necked flask equipped with a stirrer, a reflux condenser, a thermometer, and a dropping funnel. The contents of the flask were cooled in a salt-and-ice bath at $-5°$ C. with stirring. The solution of the phosphonitrile chloride oligomer mixture in monochlorobenzene which had been previously prepared was added drop by drop from the dropping funnel for 1.5 hr. When the dropping of the solution was completed, the temperature of the reaction liquid was 10° C. After completion of the dropping of the solution, the reaction was further continued at that temperature for 1 hr.

(Second Step)

Subsequently, the contents of the flask were gradually warmed in a water bath, followed by a condensation reaction at $35°\pm2°$ C. for 7 hours. The content of the remaining active chlorine in the resulting condensation reaction product was determined and was found to be 19.4% by weight.

(Third Step)

120.0 g (2.5 equivalents relative to the amount of the remaining active chlorine) of n-propyl alcohol was added drop by drop to the above reaction liquid for 1 hour, while the reaction liquid was kept at $35°\pm2°$ C. After completion of the dropping, 40.8 g (1.2 equivalents relative to the amount of the active chlorine which had been originally contained in the phosphonitrile chloride oligomer) of ammonia was blown into the contents of the flask for 4 hours, while the temperature of the contents was elevated and then kept at 50° C. or below. After completion of the blowing of ammonia, the contents of the flask were further stirred at $50°\pm2°$ C. for 6 hours, followed by a reaction at $60°\pm2°$ C. for 8 hours. The amount of the remaining active chlorine at this stage was 0.35% by weight.

The reaction was ceased, and the contents of the flask were degassed at $60°\pm2°$ C. to remove the excess ammonia. Then, 374.4 g of a mixture of the excess n-propyl alcohol, pyridine and monochlorobenzene was distilled off at the same temperature (recovery of pyridine: 98% by weight based on the amount used). 300 ml of monochlorobenzene was added to the residue of distillation. The resulting solution was washed twice with 200 ml of water. Thereafter, 50 g of anhydrous sodium sulfate was added to the solution for desiccating, followed by filtration. Monochlorobenzene was distilled off thoroughly from the resulting filtrate under a reduced pressure of 1 mmHg, thereby obtaining 129.4 g of a viscous liquid having a pale yellow color. The product was obtained in a yield of 79.4% based on the calculated value and had a viscosity of 1,250 cps at 25° C., a weight-average molecular weight of 1,470, an acid value of 2.0 mg KOH/g, and a remaining chlorine content of 0.35% by weight. In the infrared (IR) spectrum analysis of the product, an absorption around 1,000 to 870 $cm^{-1}$ of the P—O—P linkage was observed. This fact suggests that the reaction product is a propoxyphosphonitrile oligomer containing a poly(propoxyphosphonitrile oligomer). Further, the IR spectrum analysis of the product showed neither an absorption of an N-H stretching vibration of $P-NH_2$, which is known to be observed around 3330 $cm^{-1}$, nor an absorption of an N-H bending vibration of $P-NH_2$, which is known to be observed around 1,660 to 1,640 and around 1,560 $cm^{-1}$. Moreover, the nuclear magnetic resonance (NMR) analysis of the product showed the absence of a proton except for a proton derived from the propoxy group. The above facts substantiates that an amino group is absent in the product.

EXAMPLE 2

The first and second steps were conducted in the same manner as in EXAMPLE 1. After blowing of ammonia in the same manner as in the third step of Example 1, the reaction was continued at $51°\pm2°$ C. for 6 hours. Thereafter the reaction was continued at $100°\pm2°$ C. for 4 hours, while a small amount of ammonia was further blown. Thereafter, the same procedures as in EXAMPLE 1 were repeated, thereby obtaining 128.0 g of a viscous liquid having a pale yellow color. The product was obtained in a yield of 78.5% based on the calculated value and had a viscosity of 1,300 cps at 25° C., a weight-average molecular weight of 1,450, an acid value of 2.1 mg KOH/g, and a remaining chlorine content of 0.3% by weight. The NMR analysis of the product showed that the product was free from an $NH_2$ group.

EXAMPLE 3

The same procedures as in EXAMPLE 2 were repeated, except that in the first step the amount of n-propyl alcohol which had been previously put into the 1-l four-necked flask was 36.0 g (0.6 mol) (0.3 equivalent relative to the amount of the active chlorine contained in the phosphonitrile chloride oligomer), that the condensation reaction time was 3.5 hr, and that the amount of n-propyl alcohol to be added after completion of the condensation reaction was 144.0 g (2.4 mol), thereby obtaining 127.1 g of a viscous liquid having a pale yellow color. The product was obtained in a yield of 78.4% based on the calculated value and had a viscosity of 6,800 cps at 25° C., a weight-average molecular weight of 1,510, an acid value of 2.0 mg KOH/g, and a remaining chlorine content of 0.31% by weight. No $NH_2$ group was detected.

EXAMPLE 4

103.7 g (1.4 mol) (0.7 equivalent relative to the amount of the active chlorine contained in the phosphonitrile chloride oligomer) of n-butanol, 170.0 g (1.2 equivalents relative to the amount of n-butanol) of triethylamine were put into the same 1-l four-necked flask as that used in EXAMPLE 1. The contents of the flask were cooled in a slat-and-ice bath at −5° C. A solution prepared by dissolving 116.0 g of cyclic triphosphonitrile chloride in 215.4 g of monochlorobenzene was added drop by drop to the contents of the flask while stirring. The temperature of the reaction liquid was kept at 10° C. or below during the dropping. The reaction was allowed to proceed at the same temperature for 2 hours from the initiation of the dropping of the solution. Subsequently, the reaction liquid was gradually warmed in a water bath, and a condensation reaction was conducted at 35°±2° C. for 9 hours. The remaining active chlorine of the resulting condensation reaction product was 17.6% by weight. 93.0 g (1.6 mol) of allyl alcohol was added drop by drop to the reaction liquid for about 1 hour, while the reaction liquid was kept at 35°±2° C. After completion of the dropping, 40.8 g (1.2 equivalents relative to the amount of the active chlorine which had been originally contained in the phosphonitrile chloride oligomer) of ammonia was blown into the contents of the flask for 4 hours, while the temperature of the contents was elevated and then kept at 50° C. or below. After completion of the blowing of ammonia, the contents of the flask were further stirred at 50°±2° C. for 3 hours, followed by a reaction at 60°±2° C. for 9 hours.

Thereafter, the post-treatment of the resulting reaction product was conducted in the same manner as in EXAMPLE 1, thereby obtaining 115.8 g of a viscous liquid having a pale yellow color. The IR spectrum analysis of the product revealed that a carbon-carbon double bond and a P—O—P linkage were present in the product. The NMR analysis showed that the ratio of butoxy group to allyloxy group was about 3:2. Further, the IR analysis and NMR analysis revealed that the product was free from an amino group. The product had a viscosity of 980 cps at 25° C., a weight-average molecular weight of 1,390, an acid value of 2.4 mg KOH/g, and a remaining chlorine content of 0.4% by weight.

EXAMPLE 5

60.0 g (1.0 mol) of n-propanol and 144.9 g (1.4 mol) of a high-boiling picoline (alpha-picoline=0.52% by weight; beta-picoline=44.2% by weight; gamma-picoline=29.0% by weight; 2,6-lutidine=25.84% by weight; and others=0.43% by weight) were put into the same 1-l four-necked flask as used in EXAMPLE 1. The contents of the flask were cooled in a salt-and-ice bath at −5° C. 418.8 g of 27.7% by weight monochlorobenzene solution of the phosphonitrile chloride oligomer of the same kind as that used in EXAMPLE 1 was added drop by drop to the contents of the flask. The temperature of the reaction liquid was kept at 10° C. or below during the dropping. The reaction was allowed to proceed at the same temperature for 2 hours from the initiation of the dropping of the solution. Subsequently, the reaction liquid was gradually warmed in a water bath, and a condensation reaction was conducted at 35°±2° C. for 7 hours. The remaining active chlorine of the resulting condensation reaction product was 19.1% by weight. 150.3 g (1.5 mol) of cyclohexanol was added drop by drop to the reaction liquid for about 1 hr, while the reaction liquid was kept at 35°±2° C. After completion of the dropping, 40.8 g (1.2 equivalents relative to the amount of the active chlorine which had been originally contained in the phosphonitrile chloride oligomer) of ammonia was blown into the reaction liquid for 4 hr, while the temperature of the reaction liquid was elevated and then kept at 50° C. or below. After completion of the blowing of ammonia, the reaction liquid was further stirred at 50°±2° C. for 2 hr, followed by a reaction at 90°±2° C. for 5 hours.

Thereafter, the post-treatment of the resulting reaction product was conducted in the same manner as in EXAMPLE 1, thereby obtaining 118.2 g of a viscous liquid having a pale yellow color. The IR analysis of the product revealed that a P—O—P linkage was present in the product. The NMR analysis showed that the ratio of propoxy group to cyclohexanoxy group was about 1:1. Further, the IR analysis and NMR analysis revealed that the product was free from an amino group. The product had a viscosity of 1,860 cps at 25° C., a weight-average molecular weight of 1,450, an acid value of 2.1 mg KOH/g, and a remaining chlorine content of 0.35% by weight.

COMPARATIVE EXAMPLE

The steps till the completion of the second step were conducted in the same manner as in EXAMPLE 1. 120.0 g of n-propyl alcohol and 118.6 g of pyridine were then added drop by drop to the resulting mixture for about 1.5 hours, while the mixture was kept at 35°±2° C. After completion of the dropping, the reaction was allowed to proceed at 50°±2° C. for 6 hr and then at 100°±2° C. for 4 hours.

After completion of the reaction, the pH value of the reaction liquid was adjusted to 1.0, and the water phase was separated. The remaining organic phase was washed with 200 m( of 5% by weight aqueous sodium bicarbonate solution and then with 200 ml of water. 50 g of anhydrous sodium sulfate was added to the organic phase to desiccate it, followed by filtration. Monochlorobenzene was distilled off thoroughly from the resulting filtrate under a reduced pressure of 1 mmHg, thereby obtaining 68.5 g of a viscous liquid having a pale yellow color. The product was obtained in a yield of 42% based on the calculated value and had a viscosity of 480 cps at 25° C., a weight-average molecular weight of 1,180, an acid value of 14.3 mg KOH/g, and a remaining active chlorine content of 0.10% by weight. The reason why the yield of the product in this comparative example is low is believed as follows. Specifically, the P—O—P linkage formed in the second step is decomposed due to the presence of the pyridine hydrochloride under a high-temperature condition in the third step, thereby causing the formation of a compound having one or more of OH groups, and the compound is transferred to the water phase in a series of subsequent steps, i.e., pickling, washing with an aqueous sodium bicarbonate solution and washing with water. Further, the influence of the decomposition of the P—O—P linkage is reflected in a high acid value and a low weight-average molecular weight of the product as well. (This COMPARATIVE EXAMPLE corresponds to EXAMPLE 2).

What is claimed is:

1. A process for preparing a phosphonitrile compound which is substantially free from hydroxyl groups by reaction of a phosphonitrile chloride oligomer with an alcohol represented by the following general formula:

ROH wherein R is:
(1) a straight-chain or branched chain alkyl group which may be substituted by a halogen atom or an alkoxy group.
(2) a straight-chain or branched chain alkenyl group,
(3) a straight-chain or branched chain alkinyl group,
(4) an aralkyl group which may be substituted by a halogen atom, an alkyl group, or an alkoxy group, or
(5) a cycloalkyl group,
which comprises:
(1) a first step of adding said alcohol to said phosphonitrile chloride oligomer in an amount of 0.2 to 0.8 equivalent per equivalent of active chlorine contained in said phosphonitrile chloride oligomer and reacting said alcohol and said phosphonitrile chloride oligomer together in the presence of a tertiary amine in an amount equal to or greater than the amount of said alcohol at a temperature of 20° C. or below, thereby substituting 34% to 75% of the active chlorine by an RO-group,
(2) a second step of elevating the temperature of the reaction mixture obtained in the first step to cause a condensation reaction through the elimination of R-Cl at a temperature ranging from 20° C. to 60° C., and
(3) a third step of adding an alcohol to the reaction mixture obtained in the second step in an amount at least equal to the amount active chlorine which remains at the completion of the second step and reacting said alcohol with said remaining active chlorine while supplying ammonia into the reaction system, thereby substantially completely substituting remaining active chlorine by said RO-group.

2. A process according to claim 1, wherein said ammonia in the third step is supplied by blowing said ammonia into the reaction system in a gaseous state.

3. A process according to claim 1, wherein said process is conducted in an active organic solvent.

4. A process according to claim 1, wherein said alcohol is selected from the group consisting of saturated aliphatic alcohols, unsaturated aliphatic alcohols, aralkyl alcohols, alicyclic alcohols and mixtures thereof.

5. A process according to claim 1, wherein said tertiary amine is selected from the group consisting of aliphatic amines, alicyclic amines, aromatic amines, aralkyl amines, heterocyclic and mixtures thereof.

6. A process according to claim 1 wherein the first step is conducted at a temperature of about 10° C. or below.

7. A process according to claim 1, wherein said alcohol is used in the first step in an amount of 0.3 to 0.7 equivalent per equivalent of said active chlorine contained in said phosphonitrile chloride oligomer.

8. A process according to claim 1, wherein the second step is conducted at a temperature of about 30° to 35° C.

9. A process according to claim 1, wherein said alcohol is added in the third step in an amount of at least about 1.5 equivalents per equivalent of said remaining active chlorine at the stage of completion of the second step.

10. A process according to claim 3, wherein said inactive organic solvent is selected from the group consisting of benzene, toluene, xylene, monochlorobenzene, tetrahydrofuran, dioxane and mixtures thereof.

11. A process according to claim 4, wherein said saturated aliphatic alcohol is selected from the group consisting o methanol, ethanol, propanols, butanols, pentanols, octanols, trifluoroethanol and mixtures thereof.

12. A process according to claim 4, wherein said unsaturated alcohol is selected from the group consisting of allyl alcohol, propargyl alcohol and mixtures thereof.

13. A process according to claim 4, wherein said aralkyl alcohol is at least one selected from the group consisting of benzyl alcohol, chlorobenzyl alcohols, methylbenzyl alcohols, methoxybenzyl alcohols and mixtures thereof.

14. A process according to claim 4, wherein said alicyclic alcohol is cyclohexanol.

15. A process according to claim 5, wherein said aliphatic amine is selected from the group consisting of triethylamine, atripropylamine, tributylamine, trioctylamine, N-methyl-N-ethylpropylamine, N,N-diethylpropylamine and mixtures thereof.

16. A process according to claim 5, wherein said alicyclic amine is N,N-dimethylcyclohexylamine.

17. A process according to claim 5, wherein said aromatic amine is selected from the group consisting of N,N-dimethylaniline, N,N-diethylaniline, N,N-diethyltoluidine and mixtures thereof.

18. A process according to claim 5 to 14, wherein said aralkylamine is N,N-dimethylbenzylamine.

19. A process according to claim 5, wherein said heterocyclic amine is one member selected from the group consisting of pyridine, alpha-picoline, beta-picoline, gamma-picoline, 5-ethyl-2-picoline, trimethylpyridine, quinuclidine, triethylenediamine, N-methylpyrrolidine, N-methylpiperidine, and mixtures thereof.

20. A process according to claim 6, wherein said first step is conducted at a temperature of about 0° C. or below.

21. A process according to claim 2, wherein said ammonia is blown into the reaction system in the third step in an amount of about 1.1 to 1.5 equivalents per equivalent of said active chlorine contained in said phosphonitrile chloride oligomer which has been originally used.

* * * * *